(12) United States Patent
Anderson et al.

(10) Patent No.: US 6,309,409 B1
(45) Date of Patent: *Oct. 30, 2001

(54) INFLATABLE THERMAL BLANKET WITH PROVISION FOR BEING SECURED DURING USE

(75) Inventors: Thomas P. Anderson, Savage, MN (US); Mark F. Brier, Daytona Beach, FL (US)

(73) Assignee: Augustine Medical, Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/988,617

(22) Filed: Dec. 11, 1997

Related U.S. Application Data

(63) Continuation of application No. 08/531,772, filed on Sep. 21, 1995, now Pat. No. 5,773,275.

(51) Int. Cl.⁷ ....................................................... A61F 7/00
(52) U.S. Cl. ........................ 607/107; 607/114; 62/259.3; 5/423
(58) Field of Search .................................... 607/104, 107, 607/108, 114; 5/423; 62/259.3

(56) References Cited

U.S. PATENT DOCUMENTS

| 222,690 | 12/1879 | Goldschmidt . |
|---|---|---|
| 1,399,095 | 12/1921 | Webb, Sr. . |

(List continued on next page.)

FOREIGN PATENT DOCUMENTS

| 33 08 553 | 3/1983 | (DE) . |
|---|---|---|
| 0 113 420 | 11/1983 | (DE) . |
| 0 311 336 | 8/1988 | (EP) . |
| 716746 | 10/1954 | (GB) . |
| 1 334 935 | 3/1971 | (GB) . |
| 1 461 383 | 4/1973 | (GB) . |
| 1 532 219 | 6/1975 | (GB) . |
| 1 566 207 | 5/1977 | (GB) . |
| WO 85/03216 | 8/1985 | (WO) . |

OTHER PUBLICATIONS

Definition of "flap", Webster's II New Collegiate Dictionary (1995) p. 425.
Webster's Ninth New Collegiate Dictionary definition of "laminate".
Webster's Third New International Dictionary, p. 250, definition of "bond".
McGraw–Hill Encyclopedia of Science & Technology, 7th Ed., p. 713, definition of "bonding".
"Normothermia in the OR" Augustine Medical, Inc., Oct. 1989.

*Primary Examiner*—Robert L. Nasser
(74) *Attorney, Agent, or Firm*—Gray Cary Ware & Freidenrich

(57) ABSTRACT

An inflatable thermal blanket for thermal blanket and bathing a patient in a thermally-controlled inflating medium includes an inflatable thermal blanket with selectively activated ties to secure the thermal blanket to itself or hospital equipment. The inflatable thermal blanket has an outer edge and one or more substantially flat flexible flaps along the outer edge. Selected portions of the flaps include boundaries, such as perforations, defining corresponding ties. Selected ones of the ties are activated by detaching them along their respective boundaries. Then, the ties are attached to hospital equipment, or opposing ties may be attached to each other.

36 Claims, 6 Drawing Sheets

U.S. PATENT DOCUMENTS

| | | | |
|---|---|---|---|
| 1,777,982 | 10/1930 | Popp . | |
| 2,093,834 | 9/1937 | Gaugler | 128/145 |
| 2,110,022 | 3/1938 | Kliesrath | 5/334 |
| 2,122,964 | 7/1938 | Sweetland | 34/26 |
| 2,512,559 | 6/1950 | Williams | 5/347 |
| 2,601,189 | 6/1952 | Wales, Jr. | 4/160 |
| 2,706,988 | 4/1955 | Weber | 128/402 |
| 3,243,827 | 4/1966 | Kintner | 5/334 |
| 3,418,726 | 12/1968 | Sparks | 34/99 |
| 3,610,251 | 10/1971 | Sanderson | 128/379 |
| 3,610,323 | 10/1971 | Troyer | 165/46 |
| 3,691,646 | 9/1972 | Ruffolo | 34/90 |
| 3,714,947 | 2/1973 | Hardy | 128/400 |
| 3,757,366 | 9/1973 | Sacher | 5/347 |
| 4,572,188 | 2/1986 | Augustine et al. | 128/380 |
| 4,660,388 | 4/1987 | Greene, Jr. | 62/261 |
| 4,777,802 | 10/1988 | Feher | 62/3 |
| 4,807,644 | 2/1989 | Sandhaus | 128/849 |
| 4,867,230 | 9/1989 | Voss | 165/46 |
| 5,125,238 | 6/1992 | Ragan et al. . | |
| 5,184,612 | 2/1993 | Augustine | 128/400 |
| 5,300,100 | 4/1994 | Hickle et al. | 607/107 |
| 5,300,101 | 4/1994 | Augustine et al. | 607/107 |
| 5,300,102 | 4/1994 | Augustine et al. | 607/107 |
| 5,324,320 | 6/1994 | Augustine et al. | 607/107 |
| 5,336,250 | 8/1994 | Augustine | 607/107 |
| 5,343,579 | 9/1994 | Dickerhoff et al. . | |
| 5,350,417 | 9/1994 | Augustine | 607/104 |
| 5,360,439 | 11/1994 | Dickerhoff et al. | 607/104 |
| 5,384,924 | 1/1995 | Dickerhoff et al. | 5/421 |
| 5,392,847 * | 2/1995 | Stephenson | 607/107 |
| 5,405,370 | 4/1995 | Irani | 607/107 |
| 5,405,371 | 4/1995 | Augustine et al. | 607/107 |
| 5,443,488 * | 8/1995 | Namenye et al. | 607/107 |
| 5,447,531 | 9/1995 | Wood | 607/108 |
| 5,486,207 | 1/1996 | Mahawili | 607/104 |
| 5,514,169 | 5/1996 | Dickerhoff et al. . | |
| 5,545,194 | 8/1996 | Augustine | 607/108 X |
| 5,557,801 * | 9/1996 | Jakus | 607/108 |
| 5,588,968 * | 12/1996 | Sternlicht | 607/107 |
| 5,620,482 | 4/1997 | Augustine et al. | 607/107 |
| 5,658,325 * | 8/1997 | Augustine | 607/107 |
| 5,792,216 * | 8/1998 | Kappel | 607/107 |

* cited by examiner

INFLATABLE THERMAL BLANKET WITH PROVISION FOR BEING SECURED DURING USE

CROSS-REFERENCES TO RELATED APPLICATIONS

This application is continuation of U.S. Ser. No. 08/531,772, filed Sep. 21, 1995 now U.S. Pat. No. 5,773,275.

This application is related to U.S. patent application Ser. No. 08/419,718, filed on Apr. 10, 1995 in the name of Scott D. Augustine et al. The '718 application is a continuation of U.S. patent application Ser. No. 07/638,748 which issued as U.S. Pat. No. 5,405,371. The '371 patent is incorporated herein by reference.

BACKGROUND OF THE INVENTION

1. Field of the Invention

The present invention relates to inflatable thermal blankets that regulate a patient's temperature by bathing the patient in thermally-controlled air. More particularly, the invention concerns a method and apparatus for securing such a blanket during use.

2. Description of the Related Art

Augustine, et al. first described the use of temperature-controlled air to regulate the body temperature of patients, especially during and after surgery. U.S. Pat. No. 4,572,188, for example, used convective warming to prevent or treat hypothermia. In the '188 patent, temperature-controlled air is supplied by a blower unit that is connected to an airflow cover by a hose. In later-issued patents owned by the assignee of this application, the term "inflatable thermal blanket", synonymous with "airflow cover", is introduced. See, for example, U.S. Pat. No. 5,24,320, for "Thermal Blanket".

Inflatable thermal blankets assume a variety of shapes and sizes for specialized use, and include various inflatable structures that wrap around or drape over a patient. See, for example, U.S. Pat. Nos. 5,300,102 and 5,336,250. The mechanism for delivering heated air to a patient has also been expanded, beyond inflatable blankets, to include self-supporting tubes and plenums. See, for example, U.S. Pat. Nos. 5,300,101 and 5,350,417.

For ease of description, the various inflatable mechanisms for delivering a flow of temperature-controlled air to bathe a patient are referred to herein as "inflatable thermal blankets" (or, "thermal blankets"). Patient-warming systems that use inflatable thermal blankets such as these may be collectively referred to as "convective warming systems." The basic convective warming system includes a heater/blower unit, an inflatable thermal blanket, and a flexible delivery hose connecting the two. These convective warming systems provide acknowledged clinical benefits.

Various embodiments of known inflatable thermal blankets have used strips of adhesive tape to prevent a blanket moving with respect to a patient. The adhesive strips man also be used to help control the flow of the thermally-controlled air, e.g. to ensure even distribution of the temperature-controlled air, or to prevent migration of the air toward a care site. Typically, the adhesive strips adhere the thermal blanket to the patient or to a nearby piece of equipment, such as a hospital bed or operating table. In many such applications, adhesive strips have performed satisfactorily.

Nonetheless, in certain situations, patients and medical personnel alike would benefit from a different mechanism for securing an inflatable thermal blanket. In particular, some especially cost-sensitive applications require a thermal blanket that can be secured in place without additional supplies, such as adhesive strips. Also, some applications may necessitate a securing mechanism that does not leave sticky adhesive residue on hospital equipment, as adhesive strips can. Further, some users may desire a way to more quickly and conveniently secure the thermal blanket.

Therefore, significant benefits would be realized with an inflatable thermal blanket that can be quickly, efficiently, and conveniently secured in place.

SUMMARY OF THE INVENTION

Broadly, the present invention concerns an inflatable thermal blanket for covering and bathing, a patient in thermally-controlled inflating air, where selectively operated ties are used to secure the thermal blanket during use. The thermal blanket comprises an inflatable thermal blanket with a periphery and one or more substantially flat flexible flaps along the periphery. In one example, the flaps may comprise portions of a peripheral seal between a base layer and an overlaying layer.

One or more of the flaps include boundaries, such as perforations, defining ties. Selected ones of the ties are operated by detaching them from the thermal blanket along their respective boundaries. Then, individual ties may be tied to hospital equipment, or opposing ties may be brought together and tied to each other, thereby securing the inflatable thermal blanket in place.

The invention affords its users with a number of distinct advantages. For example, due to the selectively detachable ties, the thermal blanket of the invention is self-restraining—the blanket can be secured in place without any additional materials, such as adhesive tape. By avoiding the use of adhesive tape, the invention also avoids the damage or residue sometimes caused by adhesives. Users of the present invention will also recognize that the present invention is convenient, since its ties need not be activated until the user desires. The present invention also provides a number of other advantages, which are apparent from the detailed description that follows.

BRIEF DESCRIPTION OF THE DRAWINGS

The nature, objects, and advantages of the invention will become more apparent to those skilled in the art after considering the following detailed description in connection with the accompanying drawings, in which like reference numerals designate like parts throughout, wherein.

DETAILED DESCRIPTION OF THE PREFERRED EMBODIMENTS STRUCTURE

General Constructions

Figure 1:
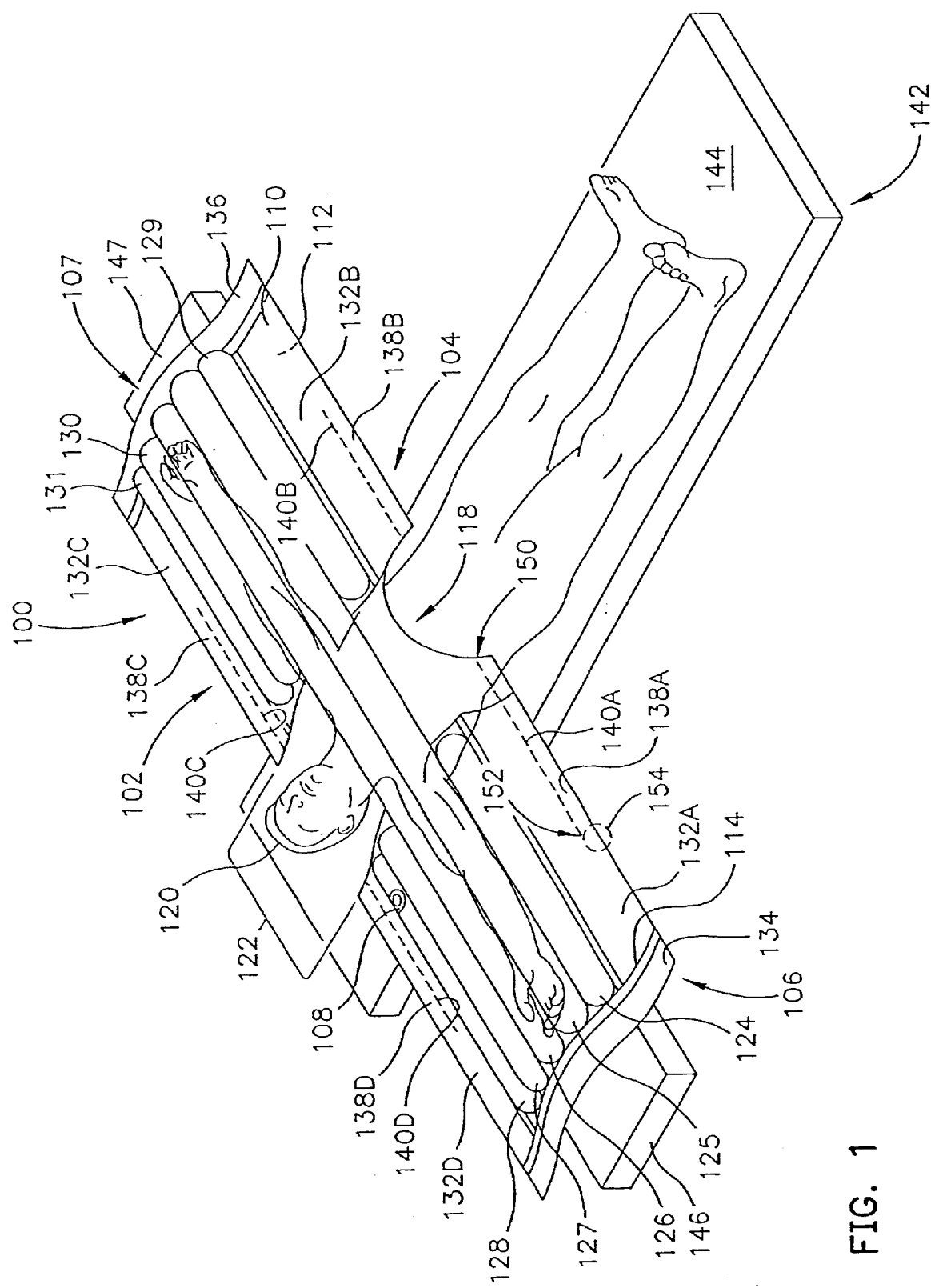
FIG. 1 is a perspective view of an inflatable thermal blanket pursuant to the invention, with unseparated ties.

FIG. 1 illustrates a specific example of the present invention, in the form of an "upper body" inflatable thermal blanket 100. The thermal blanket 100 includes a first end 102, a second end 104, and a pair of sides 106–107. The thermal blanket 100 also includes an inflating inlet cuff 108, which may be connected to a tube (not shown) leading to an external heater/blower unit (not shown). Together, the tube and heater/blower unit provide a heated airstream to inflate the thermal blanket 100. The blower unit may comprise a machine illustrated in one of the following U.S. patent applications, each of which is incorporated hereby by reference: Ser. No. 08/383,880, filed on Feb. 6, 1995, entitled "Source of Inflating Medium with Active Noise Cancellation for an Inflatable Thermal Care Apparatus" in the name of Scott D. Augustine, and Ser. No. 08/242,780, filed on May 16, 1994, entitled "Low Noise Air Blower Unit" in the name of Randall C. Arnold.

The thermal blanket 100 includes an overlying layer 110 and a base layer 112. The base layer 112 preferably includes an underside layer formed from flexible material capable of bonding to a layer of heat-sealable plastic. For instance, the base layer 112 may comprise a stratum of fibrous material pre-laminated with a layer of heat-sealable plastic.

The overlying layer 110 preferably comprises a sheet of plastic heat sealed to the base layer 112 at multiple attachment points, such as the seam 114, which provide an array of multiple inflatable chambers 124–131. In the preferred embodiment, the seams are selectively interrupted to form passageways between adjacent chambers, such that air arriving through the cuff 108 flows into and inflates all chambers of the thermal blanket 100. The base layer includes a plurality of exhaust ports (not shown) which open through the base layer into the inflatable chambers to exhaust thermally-controlled air from the chambers 124–131 into a thermal care site (not shown) within which the patent 120 lies;. The exhaust ports may have a diameter, for example, of about 1/16 inch.

Non-Inflated and Recessed Portions

In contrast to the inflatable chambers 124–131, the thermal blanket 100 may also include a number of non-inflated or recessed portions, described as follows. For example, the thermal blanket defines a recess 118 centrally positioned at the foot end 104 of the thermal blanket 100 to accommodate the patient's torso. In the illustrated embodiment, the recess 118 is facilitated by truncated chambers 124 and 129. With the upper torso and arms of a patient 120 being thermally bathed, the recess 118 permits observation of the patient's middle torso from almost any location with respect to the thermal blanket 100. The recess 118 may be provided with a tape strip along its margin; this helps prevent loss of the inflating air about the patient's torso proximate the recess 118.

The thermal blanket 100 may also include a cutout area 122 centrally positioned at the first end 102 of the thermal blanket 100. In the illustrated embodiment, the cutout area 122 is formed by truncated chambers 127–128 and 130–131. The cutout area 122 permits observation of the patient's head and neck from almost any location with respect to the thermal blanket. It also assists in thermally thermal blanket the patient's shoulders and arms without thermal blanket the patient's face.

In addition, a head drape (not shown) may be secured to the thermal blanket 100 near the cutout area 122. The head drape, which may comprise a material such as a flexible plastic, may be placed over the patient's head to administer thermal care to the patient's face. neck, etc. One or more vents may be provided in the head drape to assist the flow of fresh inflating air past the patient's head.

Generally, the non-inflated portions of the thermal blanket 100 comprise various flaps and borders present along the periphery of the thermal blanket 100. In the illustrated embodiment, the thermal blanket 100 includes a set of four flaps 132a–132d. In one embodiment, the flaps 132a–132d comprise a substantially flat region formed by bonding the overlying layer 110 and the base layer 112. Alternatively, one or the other of the overlying and base layers 110, 112 may be truncated, with the flaps 132a–132d comprising the remaining surface 110 or 112 alone. The flaps 132a–132b are defined with respect to each other by the recess 118; similarly, the flaps 132c–132d are defined with respect to each other by the cutout area 122. The flaps 132a and 132d are positioned to oppose each other, as are the flaps 132b and 132c. The periphery of the thermal blanket 100 includes the side borders 134, 136, which comprise bonded regions of the layers 110, 112 at opposing ends of the chambers 124–131.

Retaining Strips

Figure 2:
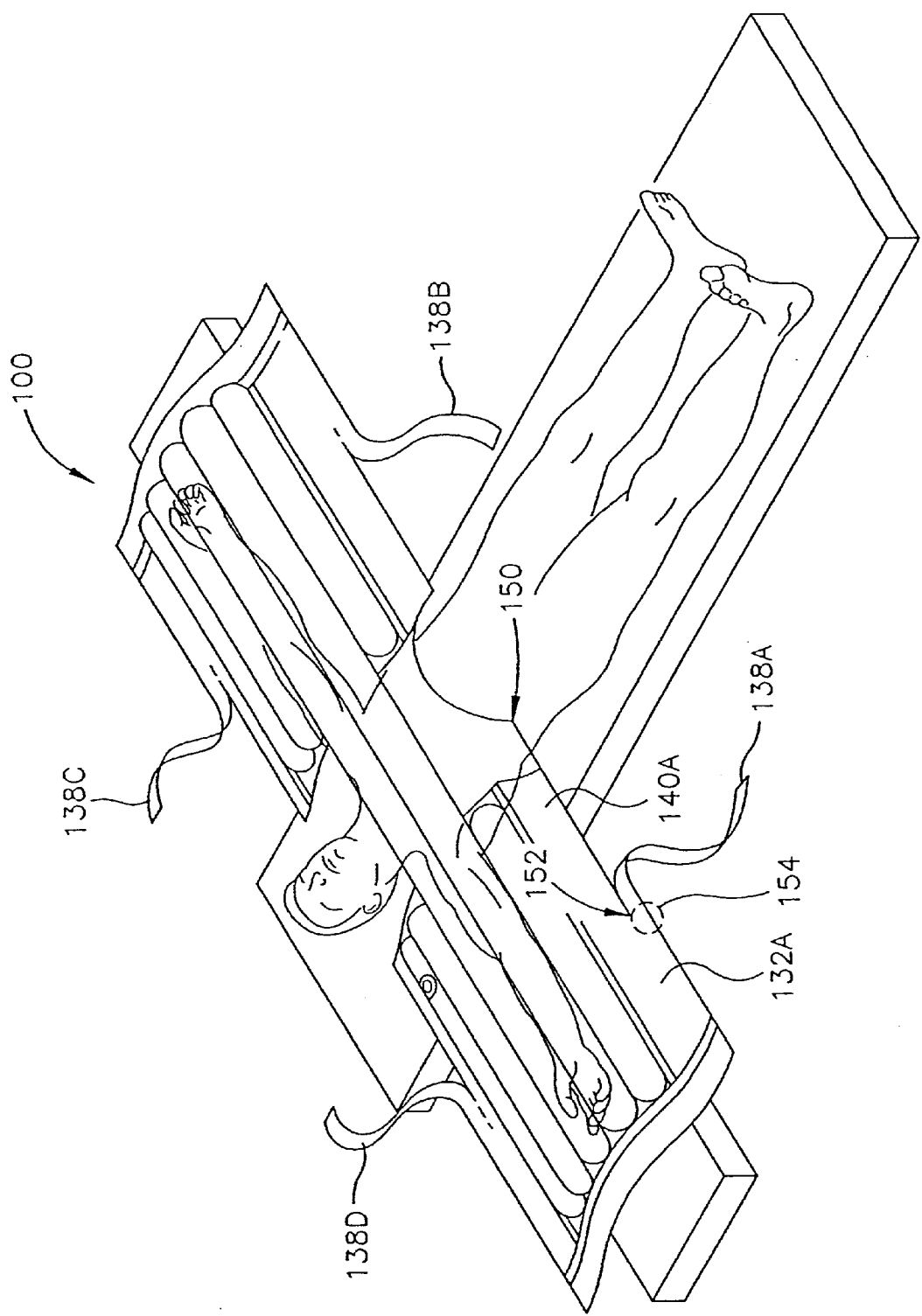
FIG. 2 is a perspective view of the inflatable thermal blanket pursuant to the invention, with ties separated but untied.
Figure 3:
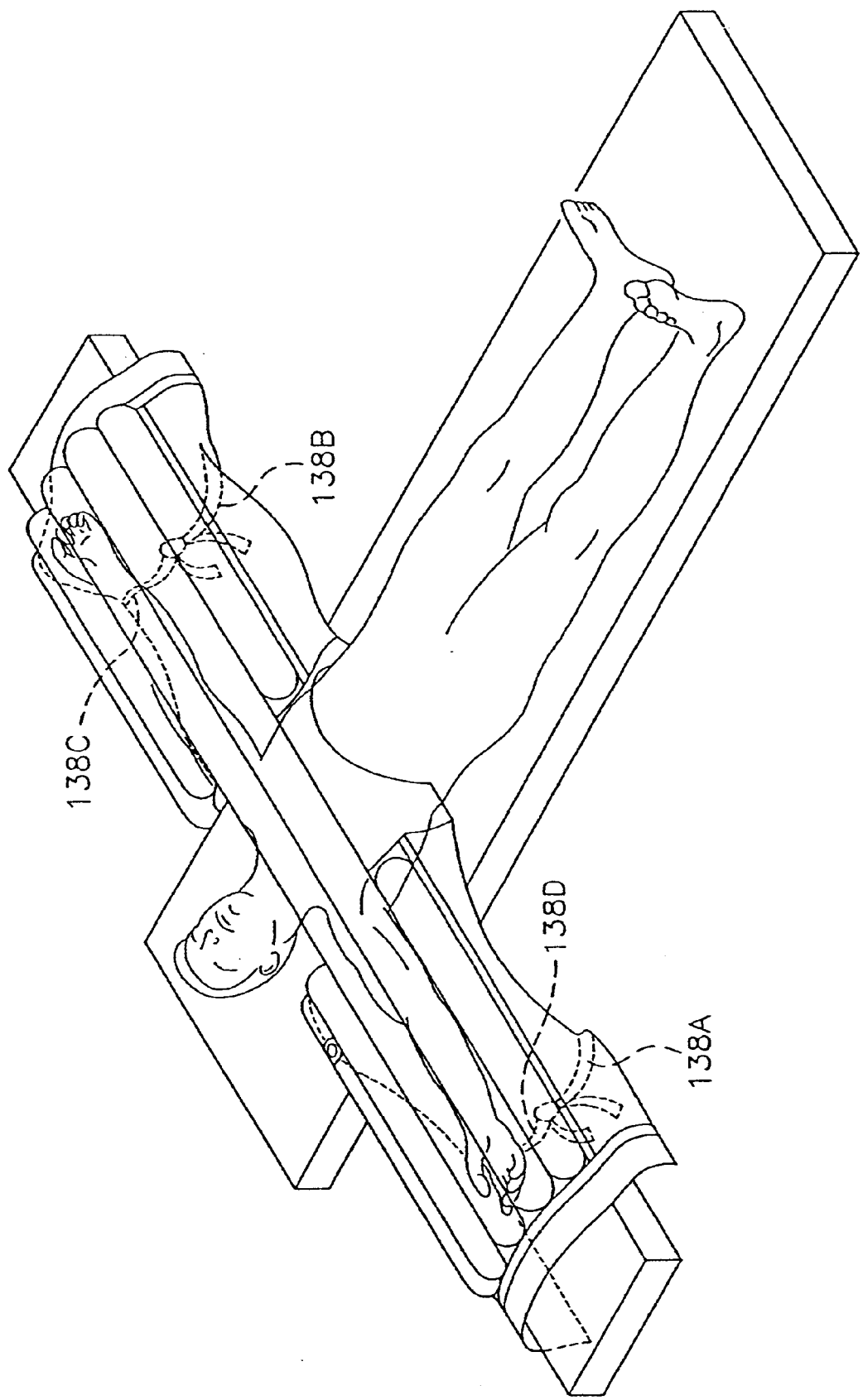
FIG. 3 is a perspective view of an inflatable thermal blanket pursuant to the invention, with ties separated and opposing strips tied together.

Refer now to FIGS. 1, 2, and 3 for an understanding of how the thermal blanket 100 is secured against movement during use. The thermal blanket 100 includes ties 138a–138d pre-defined in the flaps 132a–132d, which secure the thermal blanket during use as described below. Each tie 138a–138d comprises a relatively narrow portion of a flap 132a–132d running parallel to an outer edge of the thermal blanket 100, as defined by a boundary 140a–140d. For example, the tie 138a is defined in the flap 132a by the boundary 140a. The boundaries 140a–140d preferably comprise perforated lines that are individually severed to free a corresponding tie 138a–138d along a corresponding boundary 140a–140d. Alternatively, the boundaries 140a–140d may comprise regions of the flaps 132a–132d that are thinned, pre-cut and lightly adhered, or otherwise weakened to provide ties 138a–138d that are easily freed from their respective flaps.

Each tie 138a–138d has a sufficient length to reach and tie to an opposing tie. Preferably, each of the boundaries 140a–140d begins at an inward position of a flap 132a–132d (i.e., proximate the recess 118 or cutout area 122), and extends outward a distance toward the neighboring side 106–107. In the case of the tie 138a, for example, the boundary 140a begins at a point 150 and extends to a point 152. Thus, when the tie 138a is activated by tearing the boundary 140a from beginning 150 to end 154 as shown in FIG. 2, the activated tie 138a is largely freed from attachment to the flap 132a, but still integral with (or, securely attached to) the flap 138a at a base region 154. Preferably, the base region 154 is aligned between the patient's elbow and wrist.

After the ties 138a–138d are freed, opposing ties 138a and 138d, and opposing ties 138b and 138c are tied together, as shown in FIG. 3. The boundaries 140a–140d are preferably defined such that each strip 138a–138d is sufficiently wide to avoid any peripheral nerve damage to the patient's arm should the arm fall from the operating table.

Figure 4:
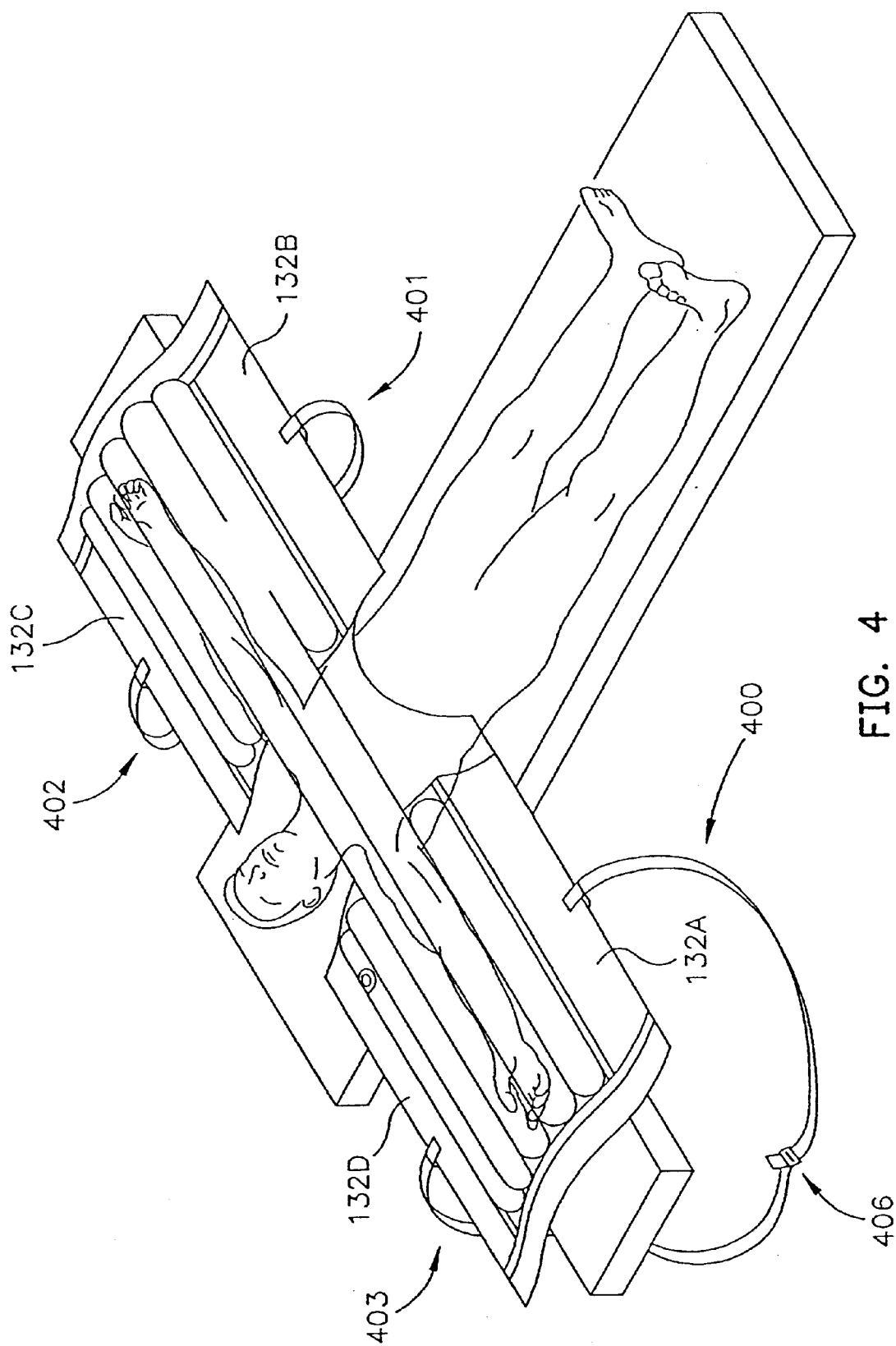
FIG. 4 is a perspective view of an inflatable thermal blanket pursuant to the invention, with a first alternate embodiment of tie.

FIG. 4 illustrates an alternate embodiment of the invention which includes ties 400–403. Each of the ties 400–403 comprises an elastic band connected to a respective flap 132a–132d by adhesive, sewing, stapling, looping through an aperture in the flap and attachment to itself, etc. In the illustrated embodiment, opposing ties are secured with a buckle 406, which is used to selectively tighten the bands. Alternatively, opposing bands may be tied together, or secured using another appropriate device. As an other alternative, opposing ties (such as 400 and 403) may comprise a single, continuous band, which can be tightened as desired by operating a buckle or another appropriate device.

Figure 5:
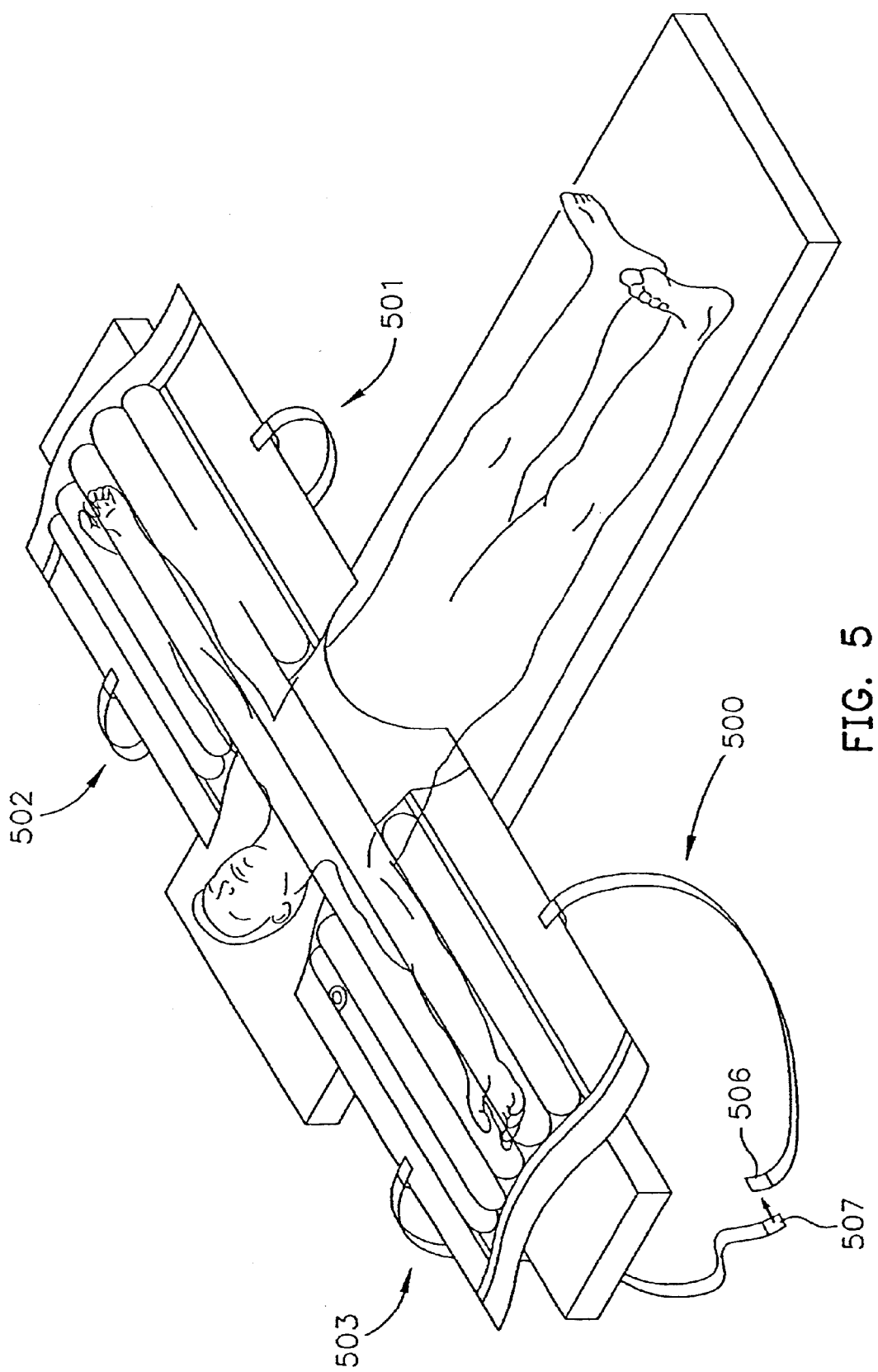
FIG. 5 is a perspective view of an inflatable thermal blanket pursuant to the invention, with a second alternate embodiment of tie.

FIG. 5 illustrates another alternate embodiment of the invention which includes ties 500–503. Each of the ties 500–503 comprises a flexible elastic or non-elastic strap, connected to a respective flap 132a–132d by adhesive, sewing, stapling, looping through an aperture in the flap and attachment to itself, etc. Unlike the embodiment of FIG. 4, however, opposing ties are secured with connectors 506–507 positioned at the respective ties' distal ends. The connectors 506–507 may comprise small adhesive patches, snaps, claps, complementary sections of hook and eye material, or another suitable device for connecting the ties. To tighten the straps, buckles (not shown) may be provided to "snug up" the straps. Alternatively, the straps may be cut with a sufficiently short length that joining the connectors 506–507 retains the thermal blanket 100 with suitable tightness.

Figure 6:
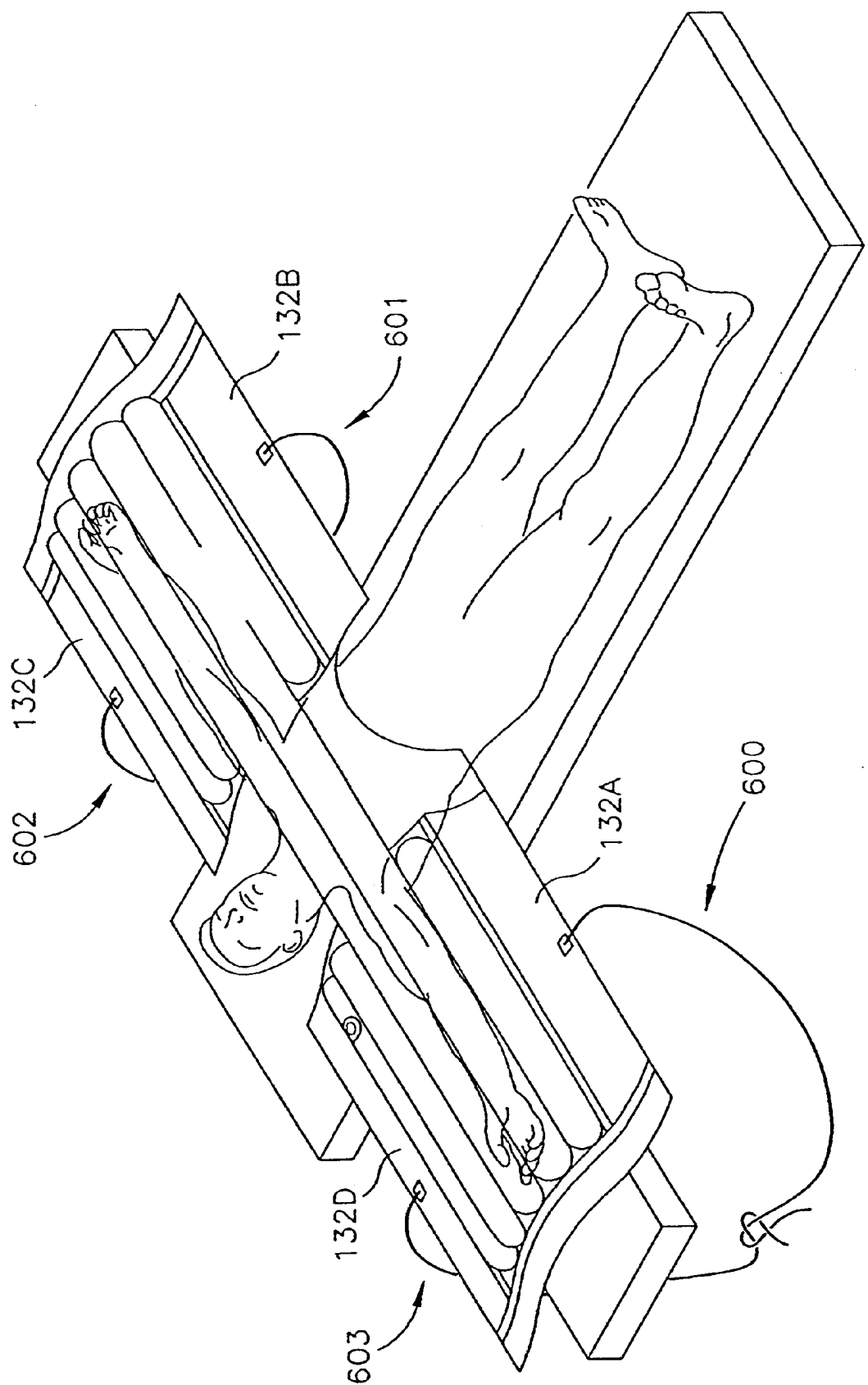
FIG. 6 is a perspective view of an inflatable thermal blanket pursuant to the invention, with a third alternate embodiment of tie.

FIG. 6 illustrates still another alternate embodiment of the invention which includes ties 600–603. Each of the ties 600–603 comprises an elastic or non-elastic string connected to a respective flap 132a–132d by adhesive, sewing, stapling, looping through an aperture in the flap and attachment to itself, etc. In this embodiment, opposing ties are connected by tying them into a knot. Alternatively, opposing ties may be connected by devices as described above, e.g. buckles, small adhesive strips, snaps, claps, complementary sections of velcro, etc.

Operation

The thermal blanket 100 may be positioned by disposing the inflatable chambers transversely across the patient's upper torso and arms so as to thermally control those areas while advantageously leaving the patient's lower torso exposed for access by medical personnel. The thermal blanket 100 may be used alone or in combination with a "lower body" inflatable thermal blanket, depending on the location of the care site. Thus, various selected portions of the patient may be selectively treated with the illustrated thermal blankets while care and treatment are rendered to other areas.

Referring to FIG. 1, the thermal blanket 100 is operated by first placing the thermal blanket 100 over the patient 120. In the illustrated embodiment, the patient 120 is in a supine position, resting upon a cruciate operating table 142. The patient's torso is aligned with a central bed portion 144 of the table 142, and the patient's arms are extended along arm boards 146–147 of the table 142. Thus, the thermal blanket 100 is positioned transversely across the patient's upper body. The bibs and drape, where applicable, are laid out over the patient as necessary.

Then, in the embodiment of FIGS. 2–3, selected ones of the ties 138a–138d are activated by detaching them along, their respective boundaries 140a–140d, as shown in FIG. 2. Each tie is tied as desired. As illustrated by the example of FIG. 3, the ties 138a–138b may be tied to opposing, ties 138d–138c (respectively). With this arrangement, each pair of opposing ties is tied about an arm board 146–147 of the operating table 142. This not only holds the thermal blanket 100 in place, but also helps retain the thermally-controlled inflating air about the patient's arms. Alternatively, the ties 138a–138d may be tied to hospital equipment such as the operating table, for example.

Next, a blower unit (not shown) is coupled to the cuff 108, and an appropriate temperature is selected using the blower unit. When the blower unit is activated, temperature-controlled air is injected into the chambers 124–131, inflating the thermal blanket 100. In the case of a hypothermic patient 120, the air preferably comprises warmed air. The chambers 124–131 exhaust the air through the exhaust ports of the base layer 112, thereby enveloping the desired regions of the patient 120 in a bath of the thermally-controlled air.

As a final measure, if desired, a conventional fabric blanket may be placed over the thermal blanket 110. During operation, the patient's temperature should be monitored regularly and the temperature setting of the blower unit adjusted accordingly.

Other Embodiments

While there have been shown what are presently considered to be preferred embodiments of the invention, it will be apparent to those skilled in the art that various chances and modifications can be made herein without departing from the scope of the invention as defined by the appended claims.

For example, although specific references are made to the use of "air," this is merely provided for an exemplary description of an inflating medium. Moreover, ordinarily skilled artisans will recognize that, instead of heating the inflating medium, it may be cooled to treat febrile patients, for instance.

Additionally, the retaining strips of the invention may be implemented in a variety of inflatable thermal blankets in addition to the upper body thermal blanket described herein. To those persons ordinarily skilled in the art with the benefit of this disclosure, for example, it will be apparent that the retaining strips of the invention may be implemented in the inflatable thermal blankets described in the following patents and patent applications, assigned to the assignee of the present application and incorporated herein by reference:

1. U.S. patent application Ser. No. 08/419,719, filed Apr. 10, 1995, entitled "Thermal Blanket", in the names of Scott D. Augustine et al.
2. U.S. patent application Ser. No. 08/315,960, filed on Sep. 30, 1994, entitled "Convertible Thermal Blanket", in the name of Scott D. Augustine.
3. U.S. Pat. No. 5,300,102, issued on Apr. 5, 1994, in the names of Scott D. Augustine et al.
4. U.S. Pat. No. 5,184,612, issued on Feb. 9, 1993, in the name of Scott D. Augustine.
5. U.S. Pat. No. 4,572,188, issued on Feb. 25, 1986, in the names of Scott D. Augustine et al.
6. U.S. Pat. No. 5,184,612, issued on Feb. 9, 1993, in the name of Scott D. Augustine (Ser. No. 890,554).
7. U.S. Pat. No. 5,324,320, issued on Jun. 28, 1994, in the names of Scott D. Augustine et al. (Ser. No. 703,592).
8. U.S. Pat. No. 5,336,250, issued on Aug. 9, 1994, in the name of Scott D. Augustine (Ser. No. 014,619).
9. U.S. Pat. No. 5,350,417, issued on Sep. 27, 1994, in the name of Scott D. Augustine (Ser. No. 063,214).
10. U.S. patent application Ser. No. 08/386,989, filed on Feb. 6, 1995, entitled "Patient Warming System with User-Configurable Access Panel." in the name of Scott D. Augustine.
11. U.S. Pat. No. 5,300,101, issued on Apr. 5, 1994.

What is claimed is:

1. An inflatable apparatus for covering and bathing a patient in a thermally-controlled inflating medium, comprising:
   an inflatable apparatus, including:
      a flexible base sheet including a plurality of exhaust ports; and a flexible overlaying sheet attached to the base sheet to define multiple inflatable chambers between the base sheet and the overlaying sheet;

said inflatable apparatus having a periphery and at least one substantially flat flexible non-inflatable flap along the periphery, a portion of said at least one flap including a boundary defining a corresponding tie for being separated from the flap by detachment along the boundary; and an inflating inlet in air communication with the inflatable chambers.

2. The apparatus of claim 1, wherein said flap comprises a substantially flat peripheral seal circumscribing coincident outer edges of the overlaying sheet and the base sheet.

3. The apparatus of claim 1, wherein the flap comprises an outer edge of the overlaying sheet.

4. The apparatus of claim 1, wherein the flap comprises an outer edge of the base sheet.

5. The apparatus of claim 1, wherein the boundary comprises a perforated line.

6. The apparatus of claim 1, wherein the boundary comprises a lightly adhered junction.

7. The apparatus of claim 1, wherein the boundary comprises a thinned region.

8. The apparatus of claim 1, wherein said inflatable chambers include elongated tube-shaped chambers.

9. The cover of claim 1, wherein the cover is substantially rectangular and the periphery defines a recess and an opposing cutout area, the periphery comprising two pairs of opposing substantially flat flexible non-inflatable flaps, each including a tie.

10. The apparatus of claim 9, including a pair of boundaries initiating at the recess and extending a first distance outward substantially along the periphery, and a pair of boundaries initiating at the cutout and extending a second distance outward substantially along the periphery.

11. The apparatus of claim 10, wherein the first and second distance are substantially equal.

12. An inflatable apparatus for covering and bathing a patient in a thermally-controlled inflating medium, comprising:

an inflatable apparatus, including:
 a flexible base sheet with a plurality of exhaust ports; and
 a flexible overlaying sheet attached to the base sheet at multiple attachment points defining multiple inflatable chambers between the base sheet and the overlaying sheet;
 said inflatable apparatus having a periphery with opposing uninflatable flaps and opposing ends;
 multiple ties disposed at separate positions in the uninflatable flaps to secure the apparatus in place; and
 an inflating inlet in communication with the inflatable chambers.

13. The apparatus of claim 12, wherein the ties comprise elastic bands.

14. The apparatus of claim 12, wherein the ties comprise strings.

15. The apparatus of claim 12, wherein the ties comprise flexible straps having distal ends affixed to connectors.

16. The apparatus of claim 15, wherein the connectors comprise selected patterns of hook and eye material.

17. The apparatus of claim 15, wherein the connectors comprise adhesive patches.

18. A method of operating an inflatable apparatus to cover and bathe a patient in a thermally-controlled inflating medium, wherein the inflatable apparatus comprises multiple interconnected inflatable chambers, a periphery and flexible uninflatable flaps along the periphery, wherein selected portions of said flaps include boundaries defining corresponding ties, said method comprising the steps of:

placing the inflatable apparatus over a patient;

freeing a pair of opposing ties by detaching the ties from the uninflatable flaps along respective boundaries, the ties remaining attached to the inflatable apparatus at respective tie ends;

coupling the pair of opposing ties together; and directing a stream of inflating medium into the inflatable chambers to inflate the apparatus.

19. The method of claim 18, wherein the patient is lying upon a central bed portion of a cruciate table and the patient's arms are extended along lateral arm boards of the table, and wherein the coupling step comprises the steps of bringing together opposing ties about an arm board and tying the opposing ties together.

20. The method of claim 18, wherein the directing step is performed after the coupling step.

21. The method of claim 18, wherein the directing step is performed before the coupling step.

22. The method of claim 18, wherein the boundaries comprise perforations and the freeing step comprises a step of severing selected perforated regions.

23. A method of operating an inflatable apparatus to cover and bathe a patient in a thermally-controlled inflating medium, wherein the apparatus includes multiple interconnected inflatable chambers and a periphery, wherein the apparatus further includes opposing uninflatable flaps at said periphery which include boundaries defining corresponding ties, said method comprising the steps of:

placing the inflatable apparatus over a patient;

freeing a tie from within an uninflatable flap by detaching the tie along a boundary thereof, the tie remaining attached to the inflatable apparatus at a tie end in the uninflatable flap;

securing the tie to a fixed object separate from the apparatus; and directing a stream of inflating medium into the inflatable chambers to inflate the apparatus.

24. The method of claim 23, wherein the directing step is performed after the securing step.

25. The method of claim 23, wherein the directing step is performed before the securing step.

26. The method of claim 23, wherein the boundaries comprise perforations and the freeing step comprises a step of severing along the perforations.

27. The method of claim 23, wherein the fixed object comprises a hospital operating table.

28. The method of claim 23, wherein the fixed object comprises a hospital bed.

29. A method of operating an inflatable apparatus to cover and bathe a patient in a thermally-controlled inflating medium, wherein the apparatus comprises multiple interconnected inflatable chambers to receive the inflating air and expel the air through a plurality of exhaust ports defined in a common surface of the chambers, said apparatus having a pair of opposing outer uninflatable flaps each including multiple ties, said method comprising the steps of:

arranging a patient upon a cruciate operating table with each of the patient's arms extended laterally;

placing the inflatable apparatus over a patient's upper body in a transverse position such that the apparatus extends from one arm, across the upper body, and across the other arm;

securing the apparatus in place around a first arm by connecting ties of opposing uninflatable flaps to form a loop about said first arm;

securing the apparatus in place around a second arm by connecting opposing ties to form a loop about said second arm; and directing a stream of inflating medium into the inflatable chambers to inflate the apparatus and bathe the patient in the thermally-treated inflating air.

30. The method of claim 29, wherein the ties comprise elastic bands and each securing step comprises the steps of placing the elastic bands around the patient's extended arms.

31. The method of claim 29, wherein the ties comprise strings and each securing step comprises the steps of placing opposing strings around the patient's extended arms and tying the opposing strings together.

32. The method of claim 29, wherein the ties comprise flexible straps having distal ends affixed to connectors, and each securing step comprises the steps of placing opposing straps around the patient's extended arms and attaching connectors of opposing straps.

33. The method of claim 32, wherein the connectors comprise selected patterns of hook and eye material, and the attaching steps comprise the steps of pressing the connectors of opposing straps together.

34. The method of claim 32, wherein the connectors comprise adhesive patches, and the attaching steps comprise the steps of pressing the connectors of opposing straps together.

35. The method of claim 29, wherein the directing step is performed after the securing steps.

36. The method of claim 29, wherein the directing step is performed before the securing steps.

* * * * *

UNITED STATES PATENT AND TRADEMARK OFFICE
CERTIFICATE OF CORRECTION

PATENT NO. : 6,309,409 B1  
DATED : October 30, 2001  
INVENTOR(S) : Anderson et al.

Page 1 of 1

It is certified that error appears in the above-identified patent and that said Letters Patent is hereby corrected as shown below:

Column 7,
Line 27, please both occurrences of "cover" and insert -- apparatus --.

Signed and Sealed this

Fourteenth Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,309,409 B1
DATED         : October 30, 2001
INVENTOR(S)   : Anderson et al.

It is certified that error appears in the above-identified patent and that said Letters Patent is hereby corrected as shown below:

<u>Column 7,</u>
Line 27, please delete both occurrences of "cover" and insert -- apparatus --.

This certificate supersedes Certificate of Correction issued May 14, 2002.

Signed and Sealed this

Twelfth Day of August, 2003

JAMES E. ROGAN
*Director of the United States Patent and Trademark Office*